(12) United States Patent
Driskill

(10) Patent No.: US 6,517,551 B1
(45) Date of Patent: Feb. 11, 2003

(54) INTRAVASCULAR FOREIGN OBJECT RETRIEVAL CATHETER

(76) Inventor: George Mark Driskill, 7379 Rocky Ford Rd., Hokes Bluff, AL (US) 35903

( * ) Notice: Subject to any disclaimer, the term of this patent is extended or adjusted under 35 U.S.C. 154(b) by 0 days.

(21) Appl. No.: 09/717,845

(22) Filed: Nov. 22, 2000

(51) Int. Cl.$^7$ ............................................... A61B 17/24
(52) U.S. Cl. ........................................ 606/113; 606/114
(58) Field of Search ............................... 606/113, 114, 606/159, 198, 200; 604/104, 105

(56) References Cited

U.S. PATENT DOCUMENTS

| | | | | |
|---|---|---|---|---|
| 5,417,697 A | * | 5/1995 | Wilk et al. ................... | 606/113 |
| 5,908,435 A | * | 6/1999 | Samuels ..................... | 606/200 |
| 5,997,547 A | * | 12/1999 | Nakao et al. ................ | 606/114 |
| 6,093,195 A | * | 7/2000 | Ouchi ........................ | 606/113 |
| 6,224,611 B1 | * | 5/2001 | Ouchi ........................ | 606/113 |

* cited by examiner

Primary Examiner—Brian L. Casler
Assistant Examiner—Kevin C. Sirmons
(74) Attorney, Agent, or Firm—George L. Williamson

(57) ABSTRACT

The present invention discloses an intravascular foreign object retrieval catheter having an elongated, flexible first outer containment catheter having a second basket catheter contained therein and having a third microcatheter contained therein and having a fourth snare wire contained therein having a loop on the end thereof. The containment catheter, the basket catheter and the microcatheter work together as coaxial tubes. The basket catheter is slidable within the containment catheter, the microcatheter is slidable within the basket catheter, and the wire is slidable within the microcatheter. The basket catheter has a containment basket on its distal end which is used to surround a foreign object whereupon the innermost wire having a loop on its end is then placed around the foreign object. Thereafter, the microcatheter is advanced along the innermost wire in order to tighten the loop around the foreign object. The microcatheter and the loop with the object contained therein are retrieved into the containment basket. The containment basket is retrieved into the containment catheter where the object may or may not be partially crushed and then the containment catheter is removed from the patient having the foreign object contained therein.

16 Claims, 4 Drawing Sheets

INTRAVASCULAR FOREIGN OBJECT RETRIEVAL CATHETER

BACKGROUND OF THE INVENTION

1. Field of the Invention

The present invention generally relates to catheters and, more particularly, is concerned with a catheter for removal of foreign objects.

2. Description of the Prior Art

Catheters have been described in the prior art. However, none of the prior art devices disclose the unique features of the present.

In U.S. Pat. No. 5,643,282, dated Jul. 1, 1997, Kieturakis disclosed a surgical instrument which is used to remove excised tissue from an insufflated anatomic cavity through a body wall overlying an endoscopic workspace. The instrument includes n elongate tubular sleeve defining an interior bore for removing a tissue. The tubular sleeve also called a snake is elastic in its transverse sectional dimension so that the interior bore can expand to accommodate the excise tissue as it is slidably withdrawn through the bore. The sleeve is not elastic in the longitudinal direction due to flexible but non-elastic longitudinal elements integrated into or on the wall of the sleeve.

In U.S. Pat. No. 4,997,435, dated Mar. 5, 1991, Demeter disclosed a percutaneous catheter with encapsulating receptacle which comprises a first catheter having a proximal and distal end, several struts attached to the distal end of the first catheter and extending distally therefrom in a cup-shaped form, a second, inner catheter received within the first, and a pocket-shaped sheath received between the several struts and opening in the distal direction, the sheath having a proximal portion secured to the distal end of the second, inner catheter, and a distal portion secured to the distal ends of the several struts, whereby rotation of the first catheter, relative the second catheter, twists and closes the distal end of the sheath. A third, outer catheter is also disclosed within which the first and second catheters, and associated struts and sheath, are receivable. Also disclosed is a method for positioning the catheter adjacent an object, or receiving the object within the sheath and enclosing the sheath about the object to facilitate treatment of the object.

In U.S. Pat. No. 5,102,415, dated Apr. 7, 1992, Guenther, et al., disclosed a triple catheter for removing of blood clots from arteries and veins which is equipped with an outer catheter that can be inserted into a blood vessel and an inner catheter with an inflatable balloon at its distal end that can be inserted into the outer catheter. The inner catheter is surrounded by an intermediate catheter also inserted into the outer catheter. The intermediate catheter has a radially expandable distal end receptacle made of an elastic mesh structure of spring wires or plastic monofilaments covered by or embedded in an elastic plastic coating. A very small puncture channel is required for the insertion of such a triple catheter through the wall of a blood vessel.

In U.S. Pat. No. 5,190,561, dated Mar. 2, 1993, Graber disclosed a tissue and organ extractor which is provided for use during laparoscopic surgical procedures. The extractor is generally rod-shaped, having a handle, an elongated shank with a central bore, and a flexible collapsible cone-shaped terminal end. The shank extends continuously between the handle and the cone-shaped terminal end. The cone-shaped end is the intra-abdominal end of the instrument and includes a generally circular open end. The handle includes a locking lever for locking a grasping instrument, which might be used to grasp tissue or organs, securely in place in relation to the extractor. In use, the surgeon inserts the extractor through a cannula and, using the grasping instrument, manipulates a tissue or organ into the open-ended, cone-shaped terminal end. The instrument used to manipulate the tissue may be locked into place in the shank of the extractor, and the extractor, instrument and tissue contained in the extractor may be removed from the abdominal cavity through the cannula. As it is being removed, the flexible cone-shaped end of the extractor envelopes and compresses the tissue contained therein.

In U.S. Pat. No. 5,312,417, dated May 17, 1994, Wilk disclosed a cannula device for use in laparoscopic surgery which includes a rigid tubular member and an expandable receiver connected to a distal end of the tubular member. The receiver portion of the cannula expands from a substantially cylindrical configuration to an expanded pocket for receiving a severed organ or organ part, thereby facilitating removal of the severed organ from a patient's abdomen during a laparoscopic surgical procedure.

In U.S. Pat. No. 5,417,697, dated May 23, 1995, Wilk, et al., disclosed a procedure for endoscopically removing a polyp which utilizes an elongate tubular member having a cup-shaped web member at a distal end portion and an electrically conductive cauterization loop inserted through the tubular member. Upon insertion of an endoscope assembly into a patient, the distal end portion of the tubular member and the cauterization loop are ejected from the distal end of the biopsy channel of the endoscope assembly. Upon a subsequent opening of the cauterization loop, the cauterization loop is placed over a polyp to be removed, the web member is then opened and suction is applied through the tubular member to entrain the polyp to the web member. Electrical current is conducted to the cauterization loop to sever the polyp from the patient, and the loop is closed. The severed polyp is held in the web member by suction and is subsequently removed from the patient.

In U.S. Pat. No. 5,423,830, dated Jun. 13, 1995, Schneebaum, et al., disclosed a method for removing a polyp from inside a patient, which comprises the steps of inserting an endoscopic insertion member into a patient, ejecting a cauterization loop from the insertion member, and maneuvering the insertion member and the cauterization loop from outside the patient to place the cauterization loop over a polyp inside the patient. A web member is ejected also from the endoscopic insertion member and is opened from a collapsed configuration to a substantially cup-shaped opened configuration having a concave inner surface. The endoscope insertion member and the opened web member are manipulated from outside the patient to juxtapose the concave inner surface of the web with the polyp, whereupon suction is applied to the web member to form a negative pressure zone between the web member and the polyp, thereby attaching the web member to the polyp in a vacuum seal. Then electrical current is conducted to the cauterization loop to sever the polyp from the patient. The web entrains the severed polyp for removal from the patient.

In U.S. Pat. No. 5,746,747, dated May 5, 1998, McKeating disclosed an instrument to perform endoscopic polypectomy having a first portion which grasps a polyp and a second portion which cuts away the polyps. The second portion is in contact with the first portion while the first portion grasps the polyp when the polyp is cut by the second portion. The first sheath member preferably contains a small grasping forcep mechanism. The second sheath member preferably contains a wire snare mechanism.

In U.S. Pat. No. 5,800,457, dated Sep. 1, 1998, Gelbfish disclosed an intravascularly deployable device in the nature of a filter for collecting intravascular debris which includes a filter or collector body expandable from a collapsed insertion configuration to an expanded use configuration. The use configuration of the filter body tapers down from a maximum cross-sectional area to a minimal cross-sectional area at a downstream end of the filter body. The filter body is provided at the downstream end with an access port so that the instrument can traverse the access port to remove debris from the filter body after disposition of the intravascularly deployable device inside a blood vessel of a patient. The access port takes the form of a sleeve or chimney which is beveled to taper down from a maximal transverse dimension at an upstream end to a minimal transverse dimension at a downstream end. The beveled or tapered sleeve is especially useful in locating or guiding the distal end of the debris removal instrument onto the downstream end of the filter body during a shifting of the instrument in the upstream direction towards the filter body.

In U.S. Pat. No. 5,908,435, dated Jun. 1, 1999, Samuels disclosed a device for removing undesirable material from a tubular structure within the human body which features a cylindrical body with a lumen therethrough. The distal portion of the body is divided into a number of flexible members. An inflatable cuff is attached to the flexible members. When the cuff is inflated, the members flex radially outwardly so that the distal opening of the lumen is expanded. An inflation tube is used to inflate and deflate the cuff by means of a syringe. An elastomeric membrane sleeve surrounds the flexible members so that the latter are contracted towards their original position when the cuff is deflated. The sleeve also prevents material from escaping between the flexible members when the cuff is inflated.

In U.S. Pat. No. 5,944,728, dated Aug. 31, 1999, Bates disclosed a surgical extractor, and related method, for removing material (such as calculi and stones) from the body which has the ability to capture and release material. The extractor has a sheath, a basket comprised of a plurality of legs that are unattached at a distal end of the basket and joined at a proximal base of the basket, and a plunger at the distal end of the sheath. The legs are movable relative to the sheath to achieve a collapsed position within the sheath and an extended position outside of the sheath in the form of an open basket. The plunger can be moved back and forth between a withdrawn position against the distal end of the sheath with the basket legs in the open position and an extended position away from the distal end of the sheath with the basket legs in a closed position. The distal ends of the legs are farther apart from each other when in the open position than when in the closed position.

While these catheters may be suitable for the purposes for which they were designed, they would not be as suitable for the purposes of the present invention, as hereinafter described.

SUMMARY OF THE INVENTION

The present invention discloses an intravascular foreign object retrieval catheter having an elongated, flexible first outer containment catheter having a second basket catheter contained therein and having a third microcatheter contained therein and having a fourth snare wire contained therein having a loop on the end thereof. The containment catheter, the basket catheter and the microcatheter work together as coaxial tubes. The basket catheter is slidable within the containment catheter, the microcatheter is slidable within the basket catheter, and the wire is slidable within the microcatheter. The basket catheter has a containment basket on its distal end which is used to surround a foreign object whereupon the innermost wire having a loop on its end is then placed around the foreign object. Thereafter, the microcatheter is advanced along the innermost wire in order to tighten the loop around the foreign object. The microcatheter and the loop with the object contained therein are retrieved into the containment basket. The containment basket is retrieved into the containment catheter where the object may or may not be partially crushed and then the containment catheter is removed from the patient having the foreign object contained therein.

An object of the present invention is to allow for the intravascular removal of foreign objects in a simple and easy fashion. A further object of the present invention is to provide a device for the highly efficient and precise removal of foreign objects from intravascular areas.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
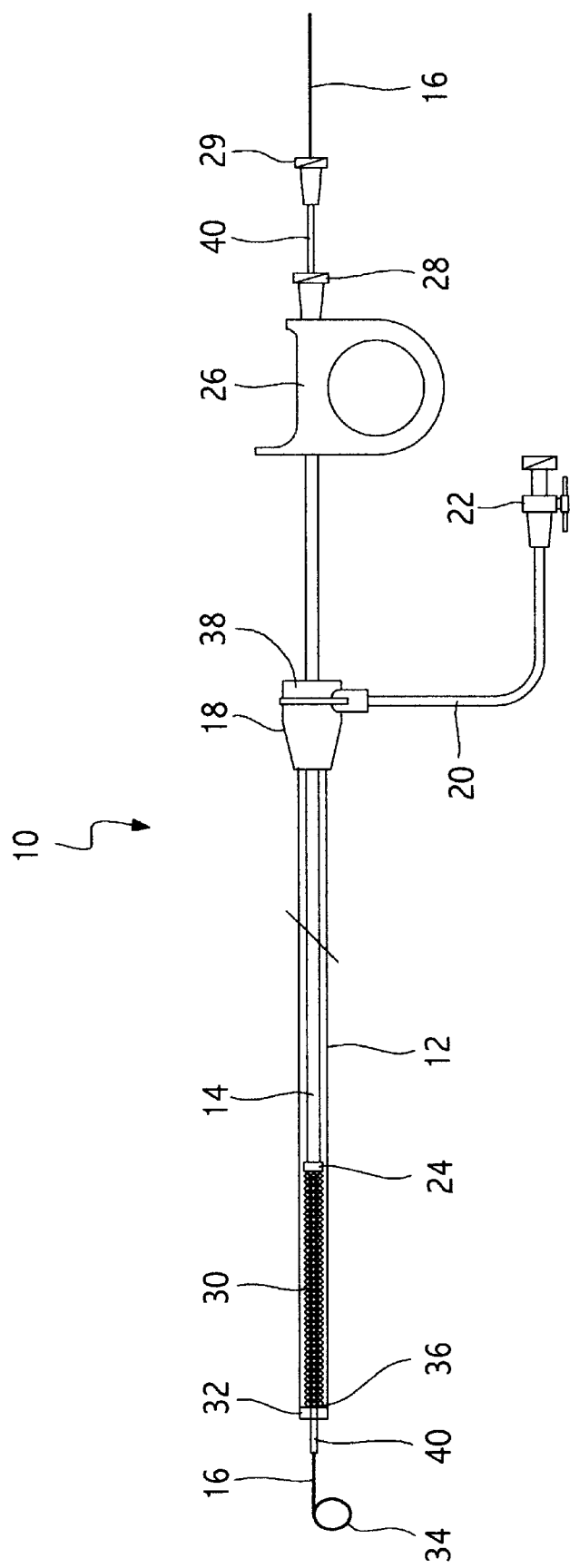
FIG. 1 is an elevation view of the present invention showing certain parts in a cut-away view.

With regard to reference numerals used, the following numbering is used throughout the drawings.

10 present invention
12 containment catheter
14 basket catheter
16 snare wire
18 valve body
20 flexible conduit
22 stop cock
24 trailing radiopaque marker band
26 grip with finger loop
28 luer-lock hub
29 luer-lock hub
30 containment basket
32 leading radiopaque marker band
34 loop
36 distal end
38 proximate end
40 microcatheter
42 end piece

DESCRIPTION OF THE PREFERRED EMBODIMENT(S)

In order that the invention may be more fully understood, it will now be described, by way of example, with reference to the accompanying drawings in which FIGS. 1 through 4 illustrate the present invention wherein an intravascular foreign object retrieval catheter is disclosed.

Turning to FIG. 1, therein is shown an elevation view of the present invention 10. Shown is the first outer containment catheter 12 along with the second basket catheter 14 slidably contained internal of the containment catheter 12 and further having a third microcatheter 40 slidably contained internal of the basket catheter 14 and furthermore having a fourth snare wire 16 slidably contained internal of the microcatheter 40. All of these members cooperate coaxially by being slidably movable within the containment catheter 12. Also shown as part of the containment catheter 12 is the valve body 18 on its proximate end 38 having a flexible conduit 20 and a stopcock 22 attached thereto whereby fluid can be passed through the stopcock 22 and the conduit 20 into valve body 18 and then into and through the containment catheter 12. Note that the containment catheter 12 has a leading radiopaque marker band 32 contained on the distal end 36 thereof. The basket catheter 14 is comprised of a stainless steel tube running from its proximate end for about one-third of its length whereupon it converges into and with a flexible plastic tube which terminates in the containment basket 30. Also shown is the gripping member 26 along with a pair of luer-lock hub 28, 29 or the like at the proximate end of the basket catheter 14 and microcatheter 40, respectively. Contained in the interior of the basket catheter 14 is the microcatheter 40. Contained in the interior of the microcatheter 40 is the sliding snare wire 16 which has a loop 34 on its distal end.

Figure 2:
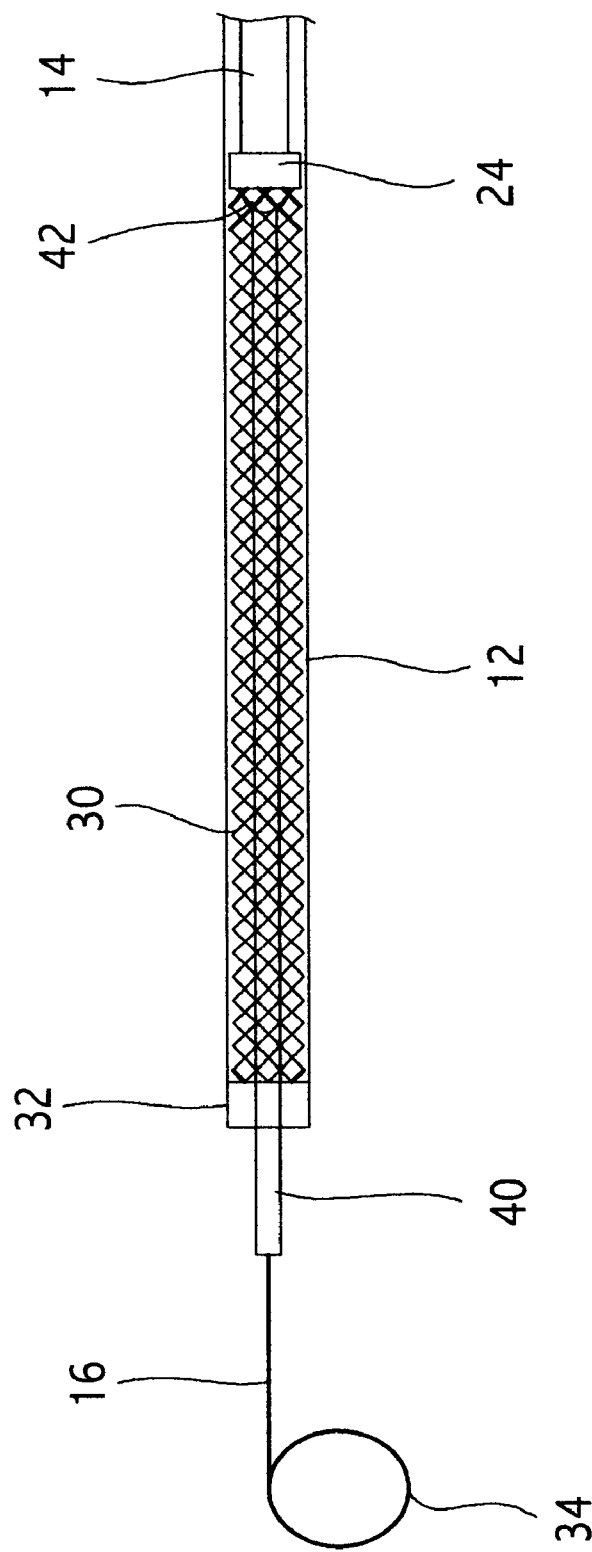
FIG. 2 is a detailed view of parts of the present invention.

Turning to FIG. 2, therein is shown a detailed view of parts of the present invention showing the trailing radiopaque marker band 24 along with the containment basket 30 showing also the inner basket catheter 14 contained within the outer containment catheter 12 and the leading radiopaque marker band 32 thereon. Also shown protruding from the basket catheter 14, through the interior of the containment basket 30 and beyond the distal end of the containment catheter 12 is the microcatheter 40 along with the sliding snare wire 16 and loop 34 protruding from its distal end. Basket catheter 14 may have a dome-like end piece 42 thereon having a central aperture therein through which the microcatheter 40 passes.

Figure 3:
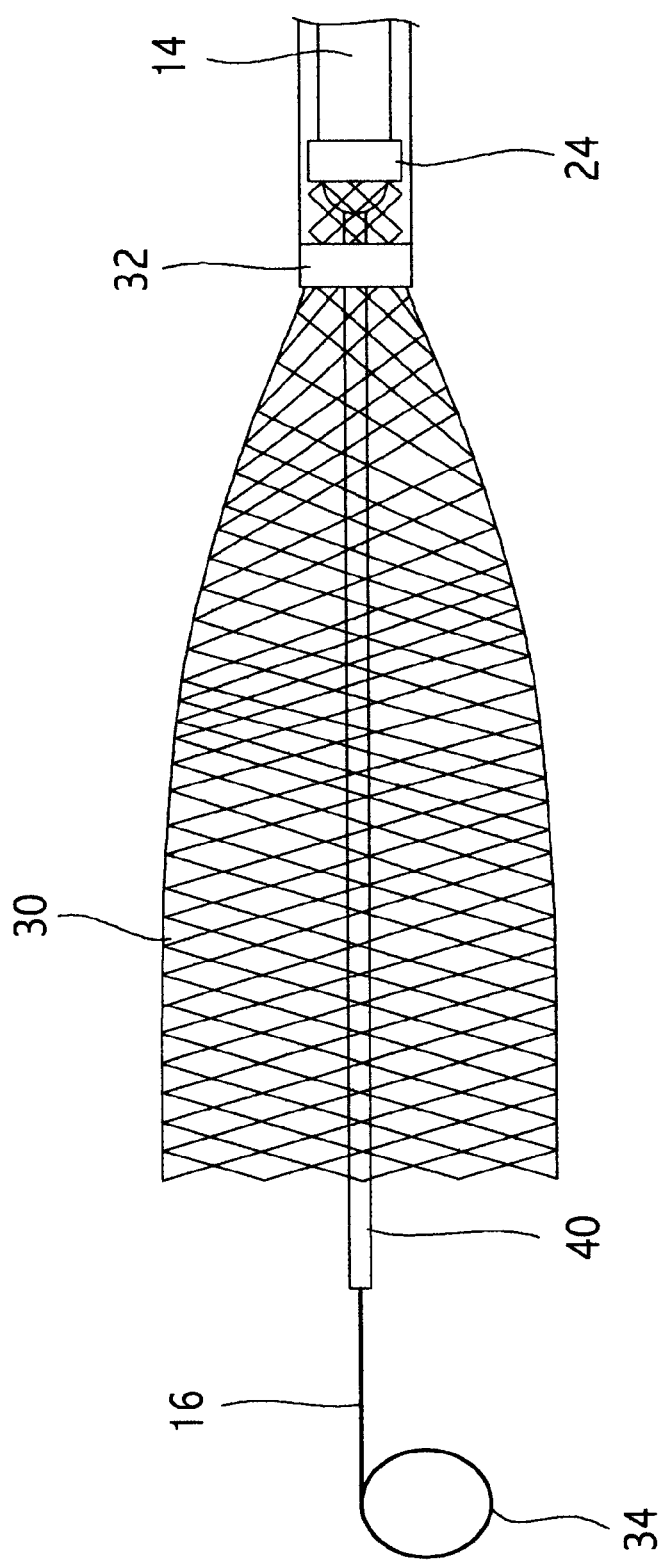
FIG. 3 is a detailed view of parts of the present invention.

Turning to FIG. 3, therein is shown a detailed view of parts of the present invention showing the expanded containment basket 30 along with the leading radiopaque marker band 32 and snare wire 16 having a loop 34 disposed on its distal end. Also shown is microcatheter 40 and trailing marker band 24.

Figure 4:
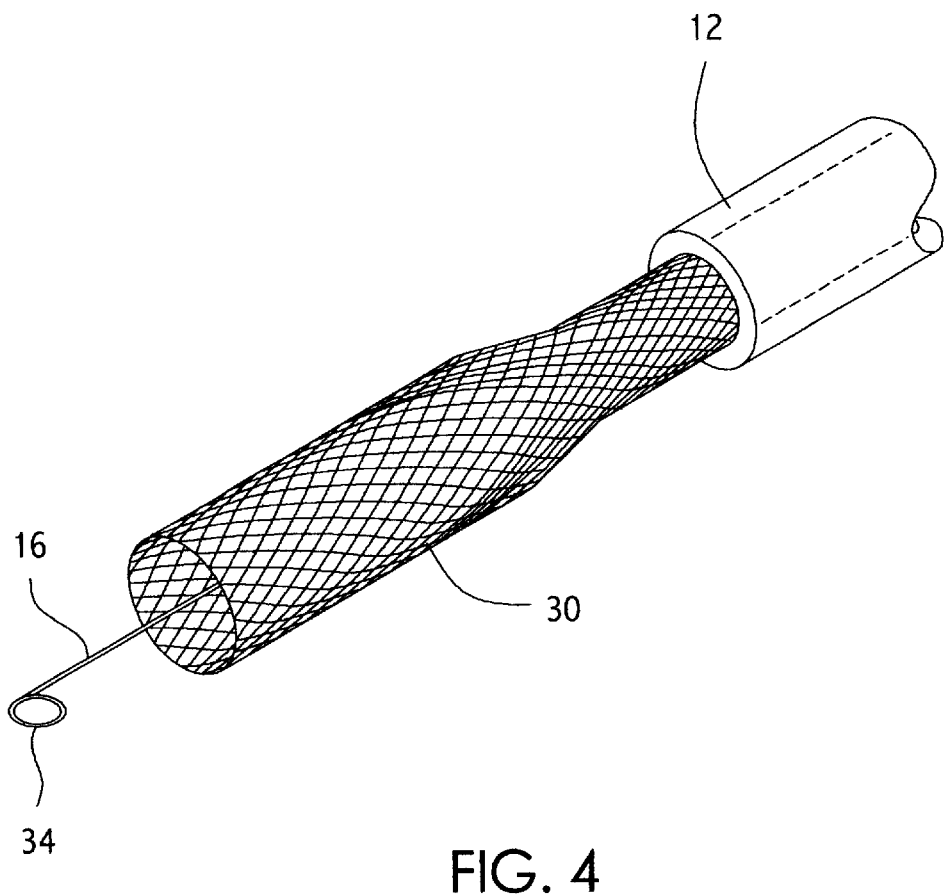
FIG. 4 is a perspective view of parts of the present invention.

Turning to FIG. 4, therein is shown the outermost containment catheter 12 having the inner containment basket 30 contained therein along with innermost inner snare wire 16 and loop 34.

With further reference to FIGS. 1–4, the containment basket 30 is fixedly attached to the basket catheter 14. The containment basket 30 is expected to be made of biomedical superalloy, monofilament wire, braided into mesh configuration which results in a basket that is flexible, self-expanding and reconstrainable. Radiopaque marker bands 24, 32 aid in placement and imaging of the present invention during foreign object retrieval. In operation, a common guide wire is inserted through the central lumen of the luer-lock hub 28 at the proximate end of the basket catheter 14 and is advanced beyond the distal end 32 of the containment catheter 12 to aid in intravascular placement. The guide wire is then removed from the central lumen of the Luer-lock hub 28 and the microcatheter 40 containing internally the sliding snare wire 16 with the loop 34 is introduced through the central lumen of the luer-lock hub 28 and advanced to the trailing radiopaque marker band 24. The containment catheter 12 is then retracted by immobilizing the basket catheter 14 via the grip apparatus 26 and gently sliding the valve body 18 along the stainless steel portion of the basket catheter 14 until the grip 26 and the valve body 18 contact. Retraction of the containment catheter 12 releases the self-expanding basket 30 from constrainment. The microcatheter 40 is then advanced through the central lumen, through the interior of the expanded containment basket 30 and beyond, to the foreign object. The sliding snare wire 16 with the loop 34 on its distal end is then advanced through the microcatheter 40. The foreign object is then encircled by the loop 34 and the microcatheter 40 is advanced along the sliding snare wire 16 until the foreign object is firmly grasped by the tightening loop 34 whereupon the foreign object will be pulled into the containment basket 30. Keeping slight tension on the loop 34, the containment basket 30 is then reconstrained by advancing the containment catheter 12 along the basket catheter 14 to its original position. This action may or may not result in a slight crushing of the foreign object. The containment catheter 12 is then removed from the intravascular area of the body.

Note that the rigid, stainless steel portion of the basket catheter 14 ends after about one-third of its length whereupon it becomes a flexible plastic tube having the containment basket 30 disposed on its distal end.

A radiopaque marker 24 is expected to be located at the point where the basket 30 and the flexible, plastic tube join and a second radiopaque marker 32 will be located on the distal end of the outer containment catheter 12. When the two markers 24, 32 touch each other, the user will know that the containment basket 30 is fully deployed.

The material that the containment basket 30 is made of is also a radiopaque material for imaging. The snare wire 16 and loop 34 are also radiopaque.

In summary, the containment basket 30 is deployed by advancing the steel tube 14 and then the snare wire 16 is advanced. The user will advance the loop, grasp the object therein, and retrieve the loop 34 containing the object therein back into the containment basket 30, and then the basket catheter 14 is retrieved back into the containment catheter 12 wherein the object is partially crushed therein.

I claim:

1. An apparatus for a catheter for removing foreign objects from intravascular areas of a body, comprising:
    a) a first outer catheter, said catheter being flexible, said catheter having a first proximate end and a second distal end;
    b) a second catheter slidably disposed internal said first outer catheter;
    c) means for a basket disposed on the distal end of said second catheter, whereby a foreign object may be contained therein and crushed upon retraction of the means for a basket into the first outer catheter;
    d) a third microcatheter slidably disposed internal said second catheter;
    e) a wire slidably disposed internal said third microcatheter;
    f) a loop disposed on the distal end of said wire for capturing foreign objects; and,
    g) wherein said first outer catheter, said second catheter, said third microcatheter, said means for a basket, said wire, and said loop operate coaxially with each other.

2. The apparatus of claim 1, wherein said first outer catheter, said second catheter, said third microcatheter, said basket, said wire, and said loop are complementarily sized to cooperate axially with each other.

3. The apparatus of claim 1, wherein said first outer catheter further comprises flexible plastic.

4. The apparatus of claim 1, wherein said second catheter further comprises stainless steel.

5. The apparatus of claim 1, wherein said second catheter further comprises flexible plastic.

6. The apparatus of claim 1, wherein said third microcatheter further comprises flexible plastic.

7. The apparatus of claim 1, wherein said means for a basket further comprises flexible mesh material.

8. The apparatus of claim 1, wherein said means for a basket further comprises monofilament wire.

9. The apparatus of claim 1, wherein said means for a basket further comprises an elongated tubular mesh.

10. The apparatus of claim 1, further comprising a grip member disposed on the proximate end of said second catheter.

11. The apparatus of claim 1, further comprising a valve body disposed on the proximate end of said first outer catheter.

12. The apparatus of claim 11, further comprising a means for a conduit connected to said valve body whereby fluid can be conveyed into said valve body.

13. The apparatus of claim 1, further comprising a means for a radiopaque marker band disposed near the distal end of said first outer catheter whereby said first catheter can be observed by fluoroscopic imaging.

14. The apparatus of claim 1, further comprising means for a radiopaque marker band disposed near the distal end of said second inner catheter whereby said second catheter can be observed by fluoroscopic imaging.

15. The apparatus of claim 1, further comprising a hub member disposed on the proximate end of said third microcatheter.

16. The apparatus of claim 1, further comprising a hub member disposed on the proximate end of said second catheter.

* * * * *